United States Patent [19]
Traina et al.

[11] Patent Number: 5,637,809
[45] Date of Patent: *Jun. 10, 1997

[54] VACUUM EXTRACTION SAMPLING SYSTEM

[75] Inventors: John E. Traina, Glenshaw; Richard Myers, Gibsonia, both of Pa.

[73] Assignee: United Sciences, Inc., Gibsonia, Pa.

[*] Notice: The term of this patent shall not extend beyond the expiration date of Pat. No. 5,458,010.

[21] Appl. No.: 456,650

[22] Filed: Jun. 2, 1995

Related U.S. Application Data

[63] Continuation-in-part of Ser. No. 218,563, Mar. 28, 1994, which is a continuation-in-part of Ser. No. 789,935, Nov. 12, 1991, Pat. No. 5,297,432.

[51] Int. Cl.$^6$ .................................................. B01L 7/00
[52] U.S. Cl. ................................. 73/864.12; 73/864.34
[58] Field of Search .............................. 73/864, 864.12, 73/864.22, 864.34, 864.35, 29.01

[56] References Cited

U.S. PATENT DOCUMENTS

| | | | |
|---|---|---|---|
| 3,817,100 | 6/1974 | Anderson | 73/213 |
| 4,484,481 | 11/1984 | Laird et al. | 73/863.12 |
| 4,596,156 | 6/1986 | Shimizi | 73/863.31 |
| 4,686,846 | 8/1987 | Aramaki | 73/23 |
| 4,823,591 | 4/1989 | Lewis | 73/3 |
| 4,883,505 | 11/1989 | Lucero | 73/864.81 |
| 4,974,455 | 12/1990 | McGowan et al. | 73/863.12 |
| 5,138,163 | 8/1992 | Buller et al. | 73/116 |
| 5,297,432 | 3/1994 | Traina et al. | 73/863.23 |
| 5,458,010 | 10/1995 | Traina et al. | 73/864.12 |

FOREIGN PATENT DOCUMENTS

0503996A1  9/1992  European Pat. Off. .

OTHER PUBLICATIONS

Richard L. Myers and Donald Vernon, "Field Experiences Using Dilution Gas Probe Techniques for Continuous Source Emission Monitoring," *Proceedings of the Controls West Conference*, pp. 347–355, submitted to the International Industrial Controls Conference and Exhibition/Controls West '85, Long Beach Convention Center, Long Beach, California, Sep. 16–18, 1985.

"Model 797: Diluting Stack Sampler," *EPM Environmental Product Brochure*.

Patent Abstrafts of Japan, vol. 009, No. 320, (P–413) 14 Dec., 1985 & JP–A–60 147 635 (Toyota Jidosha KK) 3 Aug. 1985.

Patent Abstracts of Japan, vol. 011, No. 354, (P–638) 19 Nov., 1987 & JP–A–62 133 336 (Nippon Soken, Inc., Others: 01) 16 Jun., 1987.

"Nafion Gas Sample Dryers" brochure, undated, received early 1995.

"Chapter 6: Extractive System Design," *EPA Handbook: Continuous Air Pollution Source Monitoring Systems*, pp. 6–1 to 6–18 (Jun. 1979).

"Internal Dilution System: AR–120", Anarad, Inc., Santa Barbara, California (no date).

*Primary Examiner*—Richard Chilcot
*Assistant Examiner*—Max H. Noori
*Attorney, Agent, or Firm*—Buchanan Ingersoll, P.C.; Lynn J. Alstadt

[57] ABSTRACT

A gas sampling system utilizes small sample vacuum transport to reduce the dew point of the sample. A vacuum pump maintains a substantial vacuum on the sampling system causing a sample, drawn at a rate less than a liter per minute, to be drawn and transported under partial vacuum for analysis. A dryer can be placed near the sampling probe to further reduce the dew point prior to the vacuum transport. The dew point of the sample is affected by both the dryer and the degree of vacuum transporting the gas mixture. As such, the dew point can be varied indefinitely by any reasonable combination of moisture removal by the dryer and vacuum pump strength.

26 Claims, 4 Drawing Sheets

VACUUM EXTRACTION SAMPLING SYSTEM

RELATED APPLICATION

This application is a continuation-in-part of U.S. patent application Ser. No. 08/218,563, filed Mar. 28, 1994, which is a continuation-in-part of 07/789,935, filed Nov. 12, 1991, now U.S. Pat. No. 5,297,432, issued Mar. 29, 1994.

BACKGROUND OF THE INVENTION

1. Field of the Invention

This invention generally relates to extractive gas sampling systems such as are used for analysis of process gases or fossil fuel combustive gases being vented through a stack.

2. Description of the Prior Art

An important category of extractive gas sampling relates to the compliance monitoring requirements enforced by the United States Environmental Protection Agency (EPA). Many sources of air pollution, such as fossil-fueled power plants, incinerators, metal smelters, and cement kilns, are required to monitor levels of certain gaseous species that are released into the atmosphere. These species include sulfur dioxide, nitrogen oxides, carbon monoxide, carbon dioxide and oxygen. The EPA standards for compliance monitoring systems are delineated in Volume 40 of the Code of Federal Regulations.

The gas streams to be monitored typically have certain intrinsic characteristics which complicate testing. For example, they generally contain 6% to 20% by volume of evaporated moisture, which results in a sample dew point well above that of normal ambient temperatures. Also, the gas streams often contain significant amounts of condensed moisture in the form of entrained water droplets and fog. Acid gases, such as sulfur dioxide are also generally present. Additionally, the gas streams invariably contain large quantities of particulate debris such as soot, fly-ash from fossil fuels and process material.

In order to analyze a sample for its gaseous constituents, it is necessary to remove the particulates and transport the sample to a remote location suitable for the operation of gas analysis instrumentation. For accurate measurements and for reliability of the test equipment, it is necessary to ensure that moisture and gases will not condense either in the sample probe, the sample lines, or the analyzers. However, the methods used to accomplish these goals must not themselves alter the samples in a way that negatively impacts testing accuracy.

In the past, two basic types of sampling systems have been developed for analysis of gaseous mixtures. The first type, the traditional extractive system, is shown in FIG. 1. Many vendors have supplied similar systems over the years. This system, however, has proved to have many undesirable drawbacks as described below. The second type, illustrated in FIG. 2, is a venturi dilution probe system. This type of system was developed in the 1980's primarily in response to perceived inadequacies with the traditional system. As discussed more fully below, however, the venturi probe system is also not without disadvantages.

SUMMARY OF THE INVENTION

A gas sampling system practicing the present invention utilizes a dryer adjacent a sampling probe. The dryer preferably is the type of dryer which contains a copolymer of tetrafluoroethylene and perfluoro-3,6-dioxa-4-methyl-7-octenesulfonic acid. This type of dryer enables the operator to determine how much moisture was removed from the sample. A vacuum pump maintains a substantial vacuum on a conduit which extends from the dryer to an analyzer. The dew point of the sample within the conduit line is affected by both the amount of moisture removed by the dryer and the degree of vacuum transporting the gas mixture. As such, the dew point can be varied practically indefinitely through an optimum combination of moisture removal by the dryer and vacuum pump strength.

DETAILED DESCRIPTION

Prior Art Systems

Figure 1:
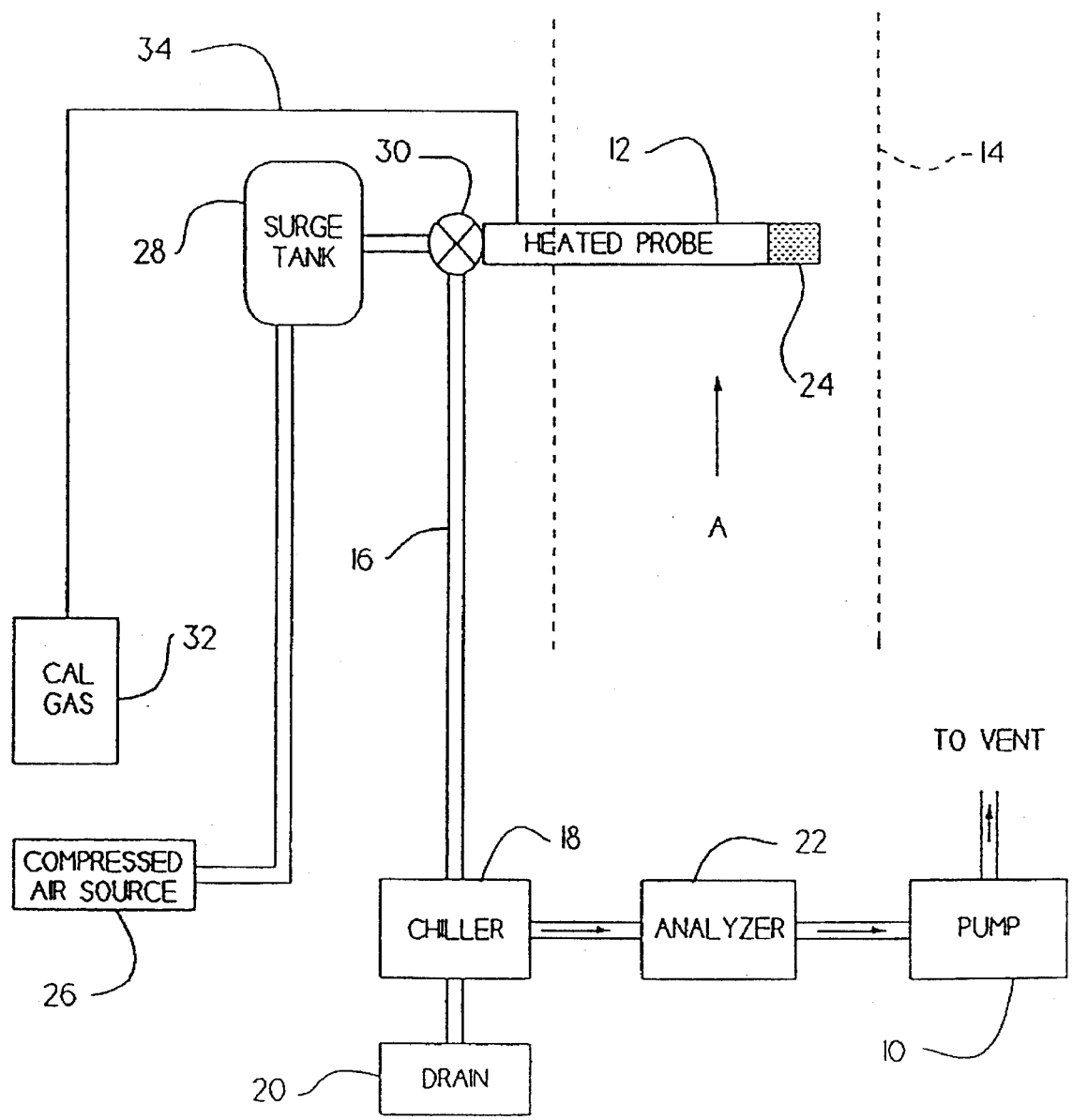
FIG. 1 is a diagram of a prior art system utilizing a heated sample line for transporting the sample.

FIG. 1 illustrates the traditional extractive system. Pump 10 draws gas through heated probe 12 from a gas stream moving within stack 14 as shown by arrow A. The sample is then transported to a remote location through a heat-traced sample line 16. Typically, probe 12 and sample line 16 are heated to about 250° F. to prevent condensation of the moisture or acid in the sample. Next, the sample is drawn through a "chiller" 18 which lowers the sample temperature to approximately 35° F. The water vapor thus condenses and is drained away at drain 20. The sample, now dry, is then reheated and transported through analyzer 22 which measures the constituents of interest. The gas sample is maintained at or near atmospheric pressure during all of this process.

A number of minor variations have been made on this basic design. Sometimes the pump is located before the analyzer. Sometimes the gas sample is diluted via the addition of nitrogen or air prior to analysis for the purpose of bringing the sample concentration within the range of the analyzers or for the purpose of reducing certain interferences within the analyzers. The analyzer and sample pump are sometimes heated so that the chiller may be omitted.

This traditional design presents a number of drawbacks and limitations. First, in order to move the sample to a remote location within an acceptable time period (EPA requires a 15 minute system response time, and process applications demand even a quicker response) the sample must be large—typically in the order of two to five liters per minute. Because the amount of particulate associated with such large samples would quickly clog any fine filter, only a coarse filter 24, such as the type constructed of sintered metal or ceramic, can be used. Even a coarse filter, however, will tend to clog every few hours in this system. To clean the filter, a blow-back design is required. For this purpose, compressed air source 26 feeds surge tank 28 which is located near ball valve 30. When valve 30 opens pressurized air in tank 28 is released, thereby purging filter 24 of impurities. Since valve 30 is continually exposed to the stack sample, however, it can develop leaks which distort the sample.

This design also requires use of large amounts of calibration ("cal") gas. Cal gas is a gas sample containing a known concentration of the species to be measured. This is used to run a calibration check on the accuracy of the measuring equipment. The EPA requires that such a calibration check be run daily using "Protocol-1" gases that may typically cost $400 for a small bottle. A similar technique using "zero gas" is sometimes employed to null the species detectors. Referring again to FIG. 1, the cal gas is fed in the traditional design from cal gas source 32 through line 34 to a location on probe 12 which is behind filter 24. Thus, deleterious effects of filter 24 such as scrubbing of sulfur dioxide by alkali particles thereon are not checked by the cal gas. In addition, a large volumetric flow of cal gas greater than the volumetric flow through tube 16 is required.

The design has a number of "weak links", which make it inherently unreliable. For example, if chiller 18 fails, analyzer 22 and pump 10 will likely be destroyed. Additionally, failure of heat tracing sample line 16 will result in condensation and contamination that can necessitate replacement of the line and all downstream plumbing. Heat traced line is significantly more expensive than unheated line. Also, since ball valve 30, analyzer 22 and pump 10 are exposed to high levels of acidic gases and to the fine particulates which permeate coarse filter 24, the service life of these components is reduced considerably.

Furthermore, when this design utilizes a chiller, a serious measurement methodology problem is presented. Specifically, gas concentrations are measured on a dry basis (i.e. with the moisture removed). Pending EPA regulations strongly favor making the concentration measurement on a wet basis (including vapor-phase moisture).

Figure 2:
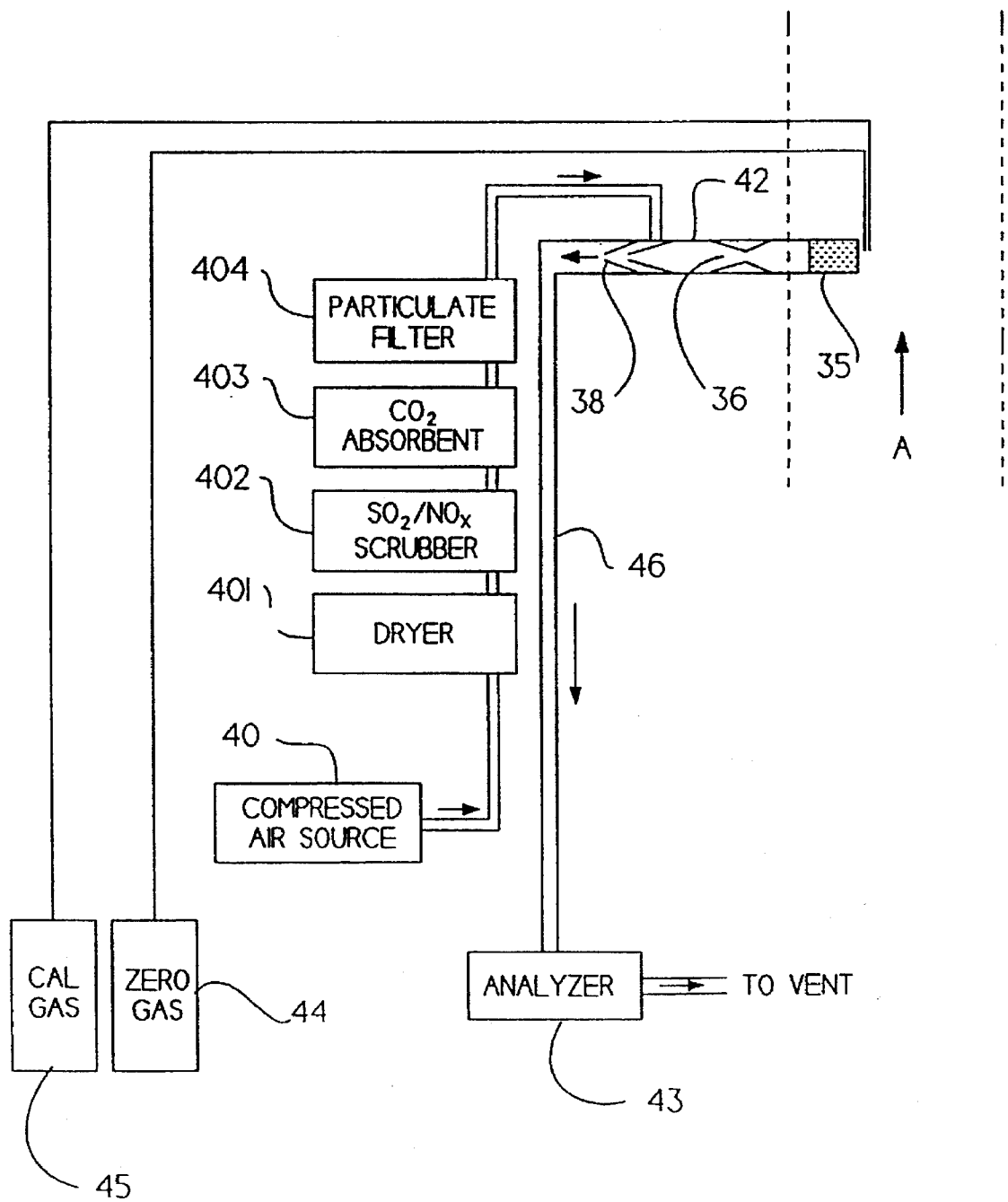
FIG. 2 is a diagram of a prior art system utilizing a dilution probe.

The second general type of prior art system, the dilution probe, is depicted as FIG. 2. In this design, the rate of stack sample extraction is considerably smaller than is the case with the traditional system of FIG. 1. Here, gas is drawn through a fine filter 35 into a device known as a "sonic orifice" or "critical-flow orifice." Sonic orifice 36 is so called because it meters a constant volumetric flow provided that a substantial vacuum exists behind the orifice. Stated another way, a pressure drop of greater than two to one (2:1) thereacross will induce a generally constant volumetric flow as metered from the upstream side of the orifice. Orifice 36 can typically be sized to permit flow as low as 20 cc per minute and as much as 200 cc per minute. Vacuum on the back side of orifice 36 is maintained by a venturi 38 which is driven by compressed air source 40. Venturi 38 also serves to provide clean, dry dilution air which lowers the sample point. The entire venturi/orifice assembly is constructed within nonheated probe 42 such that the dilution is accomplished at essentially stack temperature. The diluted sample is then sent to analyzer 43 at approximately atmospheric pressure.

This technique overcomes some of the deficiencies of the traditional extraction system. For example, cal gas 44 and zero gas 45 may be introduced upstream of filter 35 which will allow checking of deleterious filter effects. However, significant drawbacks remain. For example, because orifice 36 is a true critical-flow device, while venturi 38 is not, the dilution ratio is a function of temperature. If the process temperature varies considerably, the probe will need to be temperature controlled. Additionally, if the gas stream being sampled is fully saturated, condensation will occur on filter 35 and orifice 36 before dilution can occur. In addition, condensation will occur just downstream of the orifice 36 due to adiabatic cooling of gas passing through. In these applications, it therefore is necessary to heat the probe anyway.

Furthermore, in order to prevent condensation in unheated transport line 46, it is necessary to lower the dew point to below the expected ambient temperature. In cold climates, dilution ratios of up to 350:1 are needed. Ratios of this magnitude pose several problems. First, the concentration of the gas constituents of interest may be lowered to a level below the sensitivity of commercially available analyzers. For example, the best carbon monoxide analyzers can only measure down to five parts-per-million (5 ppm) with good accuracy. Many facilities must measure actual stack concentrations of the order of 50 ppm. Stack gas having about 50 ppm of a constituent diluted by the dilution ratio achieved in the prior art system of FIG. 2 reduces the concentration to well below 5 ppm. Another problem with high dilution ratios is that the overall system will become sensitive to minute impurities in the dilution air. As an illustration, 0.1 ppm of CO in the dilution air of the above example will be measured by the system as $(350) \times (0.1 \text{ ppm})$, the product of which is thirty-five parts per million (35 ppm). The analyzer will be unable to differentiate between this error and a comparable stack level of CO.

Moreover, the only commercially available version of this device uses a venturi that is operational only with flows of between four and seven liters per minute. This also poses several problems. For example, this large a flow of the dilution gas effectively militates against the use of bottled gas which would be prohibitively expensive and require frequent maintenance. Thus, compressed air source 40 is a compressor which utilizes the air in 9 or near the stack. That air contains particulates, $CO_2$, $SO_x$, $NO_x$ and water vapor. Consequently, one must use an array of dryers 401, scrubbers 402, absorbants 403 and filters 404 to remove contaminants from the dilution gas. Since most analyzers only require a flow in the order of 0.5 liters/minute, most of the 4–7 liters of diluted sample are wasted. Another problem is that, for a given sized orifice, there are limits to the dilution ratios that can be achieved.

Additionally, venturi 38 is generally embedded in a very expensive probe assembly. Thus, contamination, such as could occur if the orifice assembly, which is typically made of glass, would break, necessitates replacement of a very expensive piece.

Gas sampling systems have also been used to evaluate exhaust emissions from internal combustion engines. Examples of such systems are disclosed in U.S. Pat. Nos. 3,817,100 to Anderson et al.; 3,965,749 to Hadden et al.; 4,823,591 to Lewis, and 5,184,501 to Lewis et al. None of these devices are suitable for delivering a sample over long distances. They also use valve and orifice combinations to dilute the sample.

Our VDSS System

In our U.S. Pat. No. 5,297,432, we disclose a vacuum dilution extraction system or VDSS system. The system utilizes a pair of sonic orifices. One of the orifices provides a constant flow of sample gas and the other provides a constant flow of dilution gas. The resulting mixture is transported under substantial vacuum and repressurized to typically about one atmosphere prior to analysis.

Figure 3:
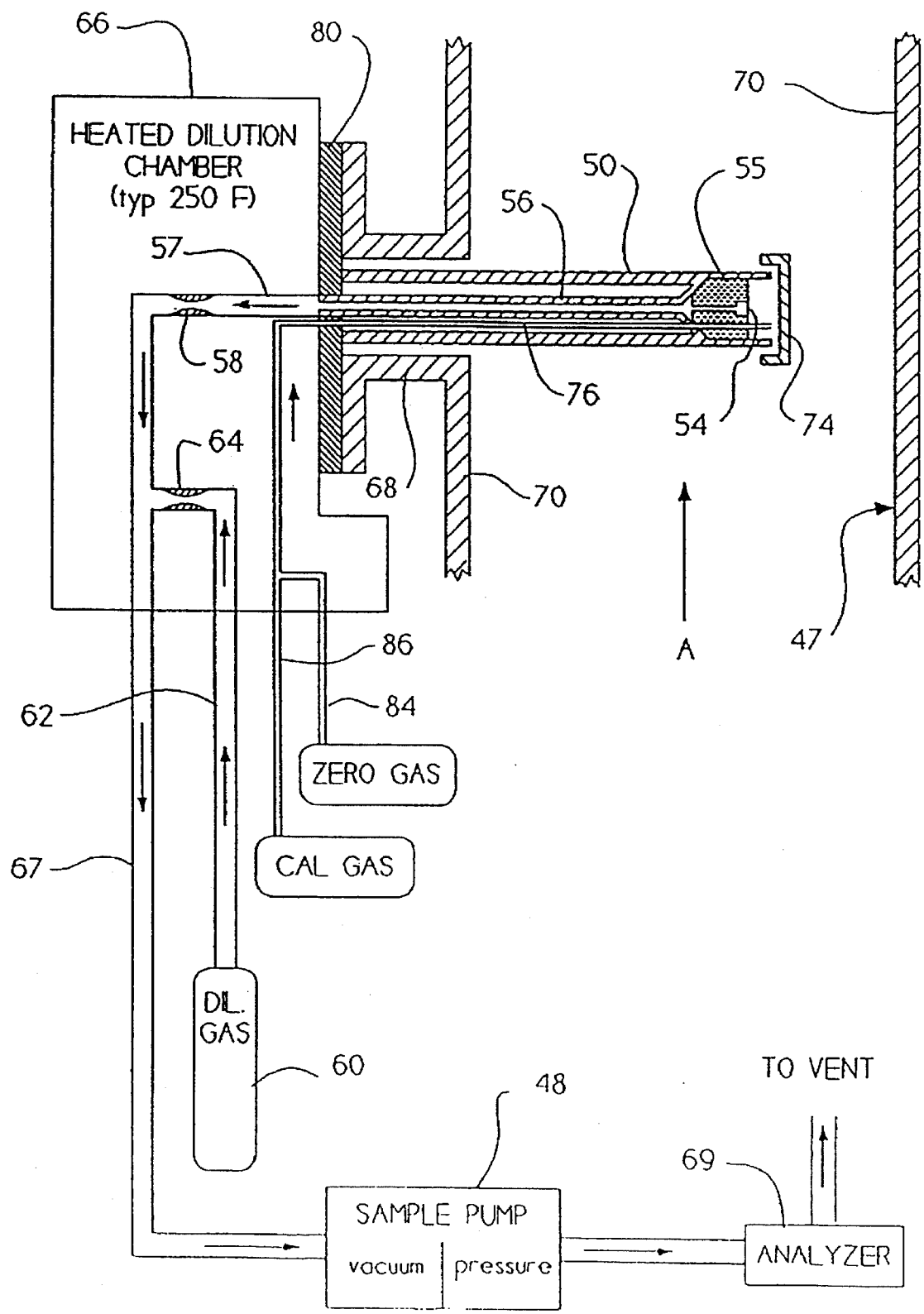
FIG. 3 is a diagram of a present preferred embodiment of the vacuum dilution extractive gas sampling system of our U.S. Pat. No. 5,297,432.

FIG. 3 illustrates a present preferred embodiment of the VDSS system. Gas from a system such as a gas stream moving within stack 47 is drawn by sample pump 48 into collection probe 50. The gas is preferably first filtered. Next, the sample passes through capillary tube 56 which is within probe 50. After leaving tube 56, the sample gas enters sample conduit 57 which has sample orifice 58 therein. Dilution gas is preferably simultaneously drawn at a controlled pressure by pump 48 from dilution gas source 60 into dilution gas conduit 62 and through dilution orifice 64 therein. Typical suitable dilution gases may be compressed air, carbon dioxide and nitrogen, depending on the sample gas and the analyzers which are desirable to be used. In order for the sample and dilution gas to be drawn simultaneously, orifices 58 and 64 are arranged in parallel. Specifically, conduits 57 and 62 intersect downstream of the orifices, forming mixing conduit 67 where mixing of the sample and dilution gas occurs. Since pump 48 maintains a substantial vacuum in conduit 67, the flow rate through orifices 57 and 62 is essentially constant. Thus, a constant dilution ratio is achieved.

Conduits 57, 62 and 67 may be constructed of any suitable inert material. Some possible materials for this purpose are glass or a corrosion resistant metal alloy such as HASTELLOY corrosion resistant alloys or corrosion resistant polymeric materials such as TEFLON material. Particularly, HASTELLOY C-22 alloy may be suitable. Orifice 58 may be as small as 0.0009 inches which corresponds to a flow rate of 4.2 cc per minute. This is much less than the minimum 20 cc per minute used in the venturi dilution system shown in FIG. 2. For a dilution ratio of 25:1, dilution orifice 64 must be five times larger in diameter than orifice 58, or 0.0045 inches in this example. This gives a flow rate of 105 cc per minute of dilution gas if the dilution gas is delivered at beneficial pressure. If the dilution gas is provided at a higher pressure, e.g., 14.7 psi, the flow will be 211 cc per minute and the dilution ratio will be 50:1. As this is a much smaller rate than the prior art, it is possible to use bottled dilution gas from gas cylinders instead of plant instrument air or compressor air. This completely eliminates problems with contamination in the dilution gas. Furthermore, by suitable selection of the orifices, it is possible to achieve any desired volumetric dilution ratio over a range of 1:1 to 250:1. For any specific set of orifices, it is possible to adjust the volumetric dilution ratio by a factor of 10, that is, over a 1:1 to 10:1 range, by simply adjusting the dilution gas pressure. Thus, the system enjoys a level of flexibility previously unattainable.

It is desirable to maintain orifices 58 and 64 in a temperature stabilized dilution chamber such as heated chamber 66. Chamber 66 is mounted engaging mounting nipple 68 which protrudes from wall 70 of stack 47. If the temperature in the dilution chamber is maintained at a fairly constant figure, the dilution ratio will be impervious to stack temperature variation. A temperature of 250° F. has been found suitable for this purpose since it is well above the dew point of most stack gases.

Typically, the dilution ratio should be chosen such that the dew point is lowered to below 30° F. Dew points below this temperature are generally not harmful to the analyzing equipment since such equipment operates at a higher temperature. Thus, condensation within the analyzer range will not occur. Generally, dilution ratios between 10:1 and 50:1 will accomplish this dew point lowering. However, a dilution ratio of even 50:1 will generally not alone lower the sample dew point enough for use in a cold climate since conduit 67 may frequently be exposed to temperatures below 30° F. For this reason, sample pump 48 transports the mixture under a substantial vacuum (0.15 atmospheric pressure) which further lowers the dew point of vapor by the factor (1/0.15)=6.67. The combination of actual volumetric dilution in vacuum transport makes it possible to lower the dew point below the coldest expected ambient temperature without actually reducing the relative concentration of the species of interest to the undesirably low levels of the prior art devices. Specifically, it is generally possible to easily lower the dew point to −25° F. using this technique.

The sample mixture next enters the vacuum side of sample pump 48 and exits the pressure side of sample pump 48 at essentially atmospheric pressure. It is not essential, however, that the analyzer 69 be placed on the pressure side of pump 48 and in other applications it may be desirable to place the analyzing equipment on the vacuum side of the pump. Thus, the species of interest are presented to analyzer 69 at a dilution ratio of only approximately 50:1 in the present example. To get the same dew point lowering with the prior art devices, the sample would have been presented to the analyzer with a dilution ratio of approximately 50:1× 6.67=333. This would be an unacceptably high dilution ratio in many cases for the reasons discussed above. Another advantage of transporting the sample under substantial vacuum is that rapid movement of the sample may be accomplished with a smaller sample rate. That is to say at reduced pressure, a sample of approximately 211 cc per minute will move through the sample line as fast as a much larger sample (211×6.67) cc/min would have moved at barometric pressure.

The preferred transport pressure for the system shown in FIG. 3 is 0.15 atmosphere or lower. Commercially available sample pumps could operate at as low as 0.075 atm. The use of more expensive sample pumps capable of achieving these lower pressures, however, is only necessary in the event that: (1) the actual dilution ratio must be kept low out of a need to operate on the range of a specific analyzer; and (2) a low ambient temperature is expected. In a warm climate it will be possible to achieve a sufficiently low dew point in conduit 67 with both a low dilution ratio and a relatively inexpensive pump. For purposes of achieving critical flow the pump only needs to achieve a vacuum of approximately 0.4 atm pressure.

There are a number of applications in which dilution systems are not a practical alternative. These include situations where it is necessary to measure oxygen (which would require use of oxygen-free dilution gas) or low levels of carbon monoxide (which taxes the lower-sensitivity channels of analyzers when the sample is excessively diluted).

Conventional "full-extraction" systems have a deserved reputation as high-maintenance devices. Analysis of the design of these systems reveals that nearly all of the maintenance issues originate from one key problem: in order to minimize lag time in transport, conventional systems draw too large a sample. Several problems result. The sample rate, which is typically 3–5 liters per minute, is too large. Consequently, the front-end filter cannot be very efficient, or it will clog. There is no way to know whether the probe blowback cleaning cycle has functioned correctly. Fine particulates penetrate the system and eventually degrade sample lines and analyzers. An excessively large sample cannot be dried at the stack probe location. This necessitates a heat-traced sample line, with disastrous downstream effects if the heat-tracing fails. If a refrigerated chiller is used to dry the sample, additional risk is introduced were the chiller to fail. If a dryer is used to dry the sample, it can be clogged with particulates. There is no way to continuously monitor the efficiency of the dryer.

The present vacuum extraction sampling system eliminates all these problems by providing a system that operates at a greatly reduced sampling rate, that can dry the sample at the stack, that provides a stack moisture measure in addition to the other required gases, and that provides complete diagnostic and interlock protection for the entire sampling train, drying system and blowback cycle.

DESCRIPTION OF THE PREFERRED EMBODIMENTS

Figure 4:
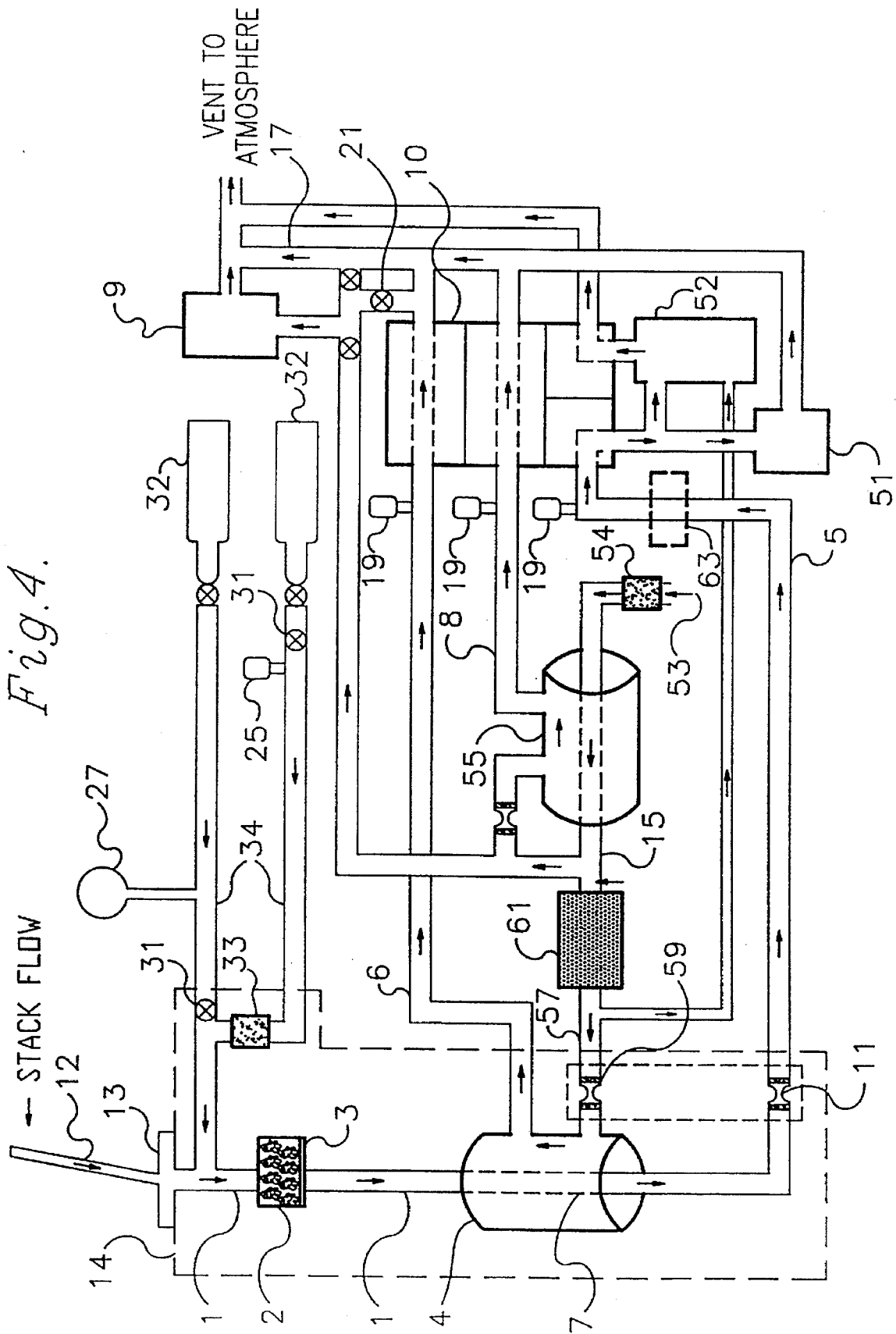
FIG. 4 is a diagram of a present preferred embodiment of the vacuum extraction sampling system of the present invention.

In our vacuum extraction sampling system shown in FIG. 4 we provide a probe 12 which extends from a flange 13 attached to the wall 14 of a duct or stack. Preferably the probe is a heated probe which has been heated to a temperature which is approximately 20° F. above the stack temperature to prevent condensation. The probe also should be inclined downward about 10° from a line perpendicular to the stack wall 14 as shown to prevent rain or entrained water from being sampled. It should be noted that there is no filter at the end of the probe and hence no opportunity for sample "scrubbing" by a filter that is not tested by the calibration gas supplied by bottles 32. The calibration air supply 32 preferably are bottles of compressed air having a known level of 02 which level has been certified by the supplier. Solenoid values 31 and a filter 33 are provided within the calibration gas supply line 34. In the present preferred system we also prefer to provide a pressure transducer 25 and a 2 liter accumulator 27.

Upon exiting the stack, the sample is drawn through sample conduit 1 having a deep-bedded glass wool filter 2, which is backed up by a porous ceramic filter 3. It is well known that a fibrous filter, which traps particles through its volume is far more efficient (>99.995%) than a "surface" filter such as is most commonly used at the end of full extraction probes. Any filter located at the probe tip must of necessity be a "surface" type; otherwise, it could not be cleaned during blowback. Because the present system utilizes a low sampling rate at about typically 150 cc./min., clogging of the filter is not a problem. At this low sampling rate, a stack grain loading of 100 mg/m$^3$ will draw only about 22 milligrams of dust into the probe per day. The filter is designed for 4 to 12 months time between filter changes for gas-fired applications, and 1 to 3 months for dirtier applications. The filter cartridge can be changed in a few minutes, without the need for stopping the sample pump.

The calibration gas for the system passes through the main sample filter 2, thereby providing a more comprehensive system check that is possible via traditional probes that have a filter at the probe tip. All factors that could affect the stack reading, including scrubbing in the filter, leaks in the transport system, and drift in the analyzers, are checked during the calibration cycle.

The normal calibration cycle starts with a blowback cycle whereby a 2-liter accumulator of compressed air is blown through the probe in a few seconds, blowing out any small accumulation of dust that may be settled in the probe since the last calibration cycle.

Note that there is a pressure transducer 25 in the calibration span line 34. This device serves two purposes. First, it is used to verify that following the blowback cycle, the pressure has dropped to the normal stack level in the expected time. This verifies that the probe is not clogged. Second, it is used in the normal sampling mode to monitor the stack pressure.

The sample which is drawn by the probe 12 passes from the filters 2 and 3 into a dryer 4. We prefer to use a dryer which contains a copolymer of tetrafluroethylene and perfluoro-3,6-dioxa-4-methyl-7-octene-sulfonic acid. This type of dryer will remove known quantities of moisture from a sample stream. Such a dryer is commercially available and sold under the trademark "PermaPure" by Perma Pure, Inc.

A sample stream is drawn into the system by vacuum pump 10 connected to the dryer 4 through conduit 5 containing sonic orifice 11. Sonic orifice 11 is sized to provide a small sample flow rate of between 5 cc. to 250 cc. per minute. For stack gas sampling we prefer a sampling rate of 150 cc./min. Conduit 5 is connected to the $O_2$ and NOx analyzers 51 and 52. In nearly all applications these analyzers operate continuously analyzing the small sample drawn by the sampling system. We prefer that the pump draw sufficient vacuum to create a pressure of approximately 0.2 atmospheres. The dryer 4 preferably will lower the dew point of the sample to about 0° F. The combined effect of the dryer and the vacuum preferably will lower the dew point of the sample in the conduit 5 to less than −20° F.

There is membrane 7 within the dryer 4 through which moisture is removed from the sample. The dryer requires a flow of dry air to remove the water from the dryer. In the embodiment of FIG. 4 we provide an ambient air intake 53. Ambient air enters intake 53 and passes through a particulate filter 54 and sonic orifice 59 into dryer 55. Dryer 55 can be the same type of dryer as the dryer 4 which is used in the sample intake line 5. Dry air from dryer 55 is directed through an indicating back up desiccator 61 to the moisture removal side of dryer 4. We prefer to set the dryer 55 to dry the filtered ambient air to 10° F. so that after passing through the indicating desiccator 61, the dew point of the air stream entering dryer 4 is at a preselected level, preferably, −100° F. Use of the dryer 55 prior to the indicating desiccator 61 reduces the replacement interval for the indicating desiccator 61 from every few days without the dryer to only a few times per year with the dryer. We provide a dew point monitor 9 connected by valve 21 to conduit 6 to measure the dew point of the air stream from dryer 4 which contains the moisture that the dryer 4 has removed from the sample stream. From this information it is a simple matter to calculate the amount of moisture that the dryer 4 has removed from the sample stream and thereby determine the moisture content of the stack gasses which have been sampled. Valves are also provided to connect the dew point monitor to the dried ambient air input line 15 and exhaust conduit 17. In the preferred embodiment, the dew point analyzer can, via selection of the appropriate solenoids, monitor any one of three streams: (1) the purge stream from the dryer in conduit 5; (2) the dew point of the dried sample in conduit 17; and (3) the dew point of the air being supplied to dryer 4 through conduit 15.

The present system provides a relatively small sample of from 5 cc. to 250 cc. per minute. Typically, the system will draw about 150 cc. of stack gases per minute. The relatively small sample used by the system, along with the very high efficiency of the filter, makes it possible to dry the sample right on the stack, using a commercially available "PermaPure" dryer. Such dryers have been used on extractive systems in the past, but have had the problem of clogging due to the largevolume, semi-filtered nature of the sample. This problem is eliminated in the clean, low-flow sample provided by the present system. Typically, the sample is dried to 0° F. right at the stack, eliminating the need for heated sample lines and for refrigerated chillers on the ground.

One of the reasons that traditional extractive system required large sample rates was to reduce transmit time in the sample line. Our system accomplishes rapid sample transport by moving the system under vacuum, typically about 0.2 atmosphere. This transports the 150 cc./min. sample five times faster than it would move at barometric pressure. Using a 0.25" O. D. Teflon tube with 0.0345" wall thickness, the sample is transported at rates in excess of 125 ft./min.

Vacuum transport of the dried sample serves a second purpose. It further reduces the sample dew point. A sample that has been dried to 0° F. at atmospheric pressure will have a dew point of −28° F. at a transport pressure of 0.2 atmosphere.

Commercially available NOx and $O_2$ analyzers have a sufficiently fast response time to meet EPA requirements with sample flows of less than 100 cc/min. A greater than necessary sample flow, particularly if the larger sample is at the expense of thorough filtering, will only cause accelerated contamination of the sample cells of the analyzer. The present sampling system is designed to best match the minimal flow requirements of the analyzers.

The "PermaPure" dryer 4 on the stack can remove more than 99% of the moisture from the stack sample. The purge flow through conduit 57 is metered through a temperature-controlled orifice 59. Preferably orifice 59 and orifice 11 in sample line 5 are sized so that the sample stream flow and the dryer purge stream flow form a stable ratio. Because the purge flow through the dryer is metered and therefore known, the absolute amount of removed moisture is known. Since the stack sample rate is also known, it is straightforward for this system to calculate the stack moisture from the known amount of water removed from a known flow. It is important to know the moisture any time that a mass emission (e.g. lb/hr) is being calculated from a wet-based flow measurement and a dry-based gas concentration.

The present system maintains an ongoing self-diagnostic check of the drying system. Dry air for the stack "PermaPure" dryer 4 is produced from ambient air via a second "PermaPure" dryer 55 located in the instrument cabinet. The dew point analyzer 9, which normally monitors the stack moisture, is periodically switched to check the dryness of this purge air. It is hereby straightforward to provide a Maintenance Alert whenever the dew point of this air is out of tolerance. A canister 61 of indicating desiccant downstream of the dryer 55 provides temporary protection while the cause of dryer failure is investigated. An optional "bottle backup" can be installed that automatically switches to a bottle of dry air when needed without any interruption in stack monitoring.

A third use of the dew point analyzer 9 is for periodic checks of the dryness of the stack sample itself. If the dryness of the stack sample that is being delivered to the analyzers is ever out of specification, the sampling pump is simply shut off, and the probe is put into a zero purge mode. No other extractive sampling system provides such a comprehensive degree of protection for the analyzers and the sampling line from the deleterious effects of condensation.

Absolute pressure transducers 12 are located on the vacuum sample line 5 and on the vacuum side of each of the "PermaPure" dryer purge lines 6 and 8. Any a time that the vacuums are out of specification, it is straightforward to provide a Service Alert to the user. Any time that a measured parameter is dangerously out of specification, the pump is automatically shut off and the system is put into the zero purge condition so as to protect the analyzers from damage.

A further pressure transducer 25 is the one already described in the calibration span line 3. Any time that the probe pressure does not return to normal within a specified time, a Probe Service alert call be provided. This is not a situation that is expected to occur; inasmuch as only a tiny amount of dust will enter the heated probe during the period between blowback. In short, the present system is designed for low sample rate, corresponding low maintenance, probe blowback, a calibration check that tests the entire system, monitoring of stack moisture, monitoring of the dew point of all flowing streams; and monitoring of the pressure/vacuums of the sample and vacuum flows monitoring for probe pluggage.

In the embodiment shown in FIG. 4 we show a $NO_x$ analyzer and an $O_2$ analyzer. However, other types of analyzers such as a $CO_2$ analyzer, could be used in place of or in addition to the analyzers we have illustrated. In an alternative embodiment we can provide a mass spectrometer 63, shown in chainline in FIG. 4, in the vacuum line 5 which can detect the presence of a variety of chemical compounds in the sample. When a mass spectrometer is used we prefer that the sample be transported under vacuum at an absolute pressure of less than 20 millimeters of mercury.

The various components of our system should be made from materials which are compatible with and not adversely affected by the gases that are being sampled. Such materials include corrosion resistant metal alloys, glass, and corrosion resistant polymeric materials.

We expect that a dryer will be used in most applications of our system. However, in certain applications it may not be necessary that the dryer remove 99%, or even 90%, of the water vapor from the sample. If the sample transport conduit is not subject to extreme cold, and if a sufficiently high vacuum is used, it may not even be necessary to use a dryer at all. Commercially available vacuum pumps can draw a vacuum as low as a fraction of a millimeter of mercury absolute pressure. Thus, in some situations the vacuum pump can draw a low enough vacuum to reduce the dew point to an acceptable level without drying the sample. The essence of the present invention is that, by use of a small sample and vacuum transport, commercially available dryers may be used when needed, such that the sample may be transported through unheated conduits without the need for dilution.

Although we have shown and described certain present preferred embodiments of our vacuum sampling system, it is to be distinctly understood that our invention is not limited thereto but may be variously embodied within the scope of the following claims.

We claim:

1. An apparatus for collecting a sample stream from a system containing water vapor and at least one other gas comprising:

a) a collection probe adapted to draw the sample stream from the system;

b) a particulate filter connected to the collection probe so that the sample stream will flow therethrough;

c) a conduit connected at one end to the particulate filter and suited for connection at another end to an analyzer, the conduit having an orifice sized to permit the sample stream to flow through the conduit at a sampling rate of from 5 cc. to 250 cc. per minute; and d) at least one pump connected to the conduit for drawing a vacuum on the sample stream.

2. The apparatus of claim 1 also comprising a dryer connected to the conduit prior to the orifice for removing water from the sample stream before the sample stream is transported to an analyzer.

3. The apparatus of claim 2 wherein the dryer contains a copolymer of tetrafluoroethylene and perfluoro-3,6-dioxa-4-methyl-7-octene-sulfonic acid.

4. The apparatus of claim 2 also comprising a dryer purge line connected to the dryer and having a critical orifice therein, the critical orifice positioned within the conduit and the critical orifice positioned within the purge line being sized so that a known stable ratio is formed between purge flow and sample flow.

5. The apparatus of claim 4 also comprising means for supplying a dry air stream having a known moisture content to the dryer into which dry air stream moisture removed from the sample stream by the dryer is exhausted thereby forming a dryer exhaust stream and means for measuring moisture content of the dryer exhaust stream, both means being connected to the dryer, such that moisture content in the sample stream may be calculated from the moisture content of the dryer exhaust stream and the known stable ratio of sample flow and purge flow rates.

6. The apparatus of claim 5 wherein the means for supplying a dry air stream having a known moisture content to the dryer is at least one of a dryer having an ambient air input and a desiccant.

7. The apparatus of claim 1 also comprising an analyzer connected to the conduit.

8. The apparatus of claim 7 wherein the analyzer is able to measure at least one property of the sample stream which property is one of $O_2$ level, NOx, $SO_2$, $CO_2$ and dew point.

9. The apparatus of claim 1 wherein the at least one pump creates a pressure in the sample stream not greater than 0.40 atmospheres.

10. The apparatus of claim 1 wherein the filter is a replaceable cartridge type filter.

11. The apparatus of claim 1 wherein at least a portion of the conduit is tetrafluoroethylene.

12. The apparatus of claim 1 also comprising a pressure transducer connected to the conduit.

13. The apparatus of claim 1 also comprising a calibration gas source connected through a calibration gas conduit to the filter in a manner so that calibration gas may flow through the filter into the conduit.

14. The apparatus of claim 13 also comprising a pressure transducer connected to the calibration gas conduit.

15. The apparatus of claim 13 also comprising an accumulator connected to the calibration gas conduit.

16. A method of extractive sampling from a system containing water vapor and at least one other gas comprising the steps of:
   a) placing a sampling probe in the system;
   b) drawing a vacuum on the sampling probe to collect a sample and to induce the sample to flow from the system at a sampling rate of from 5 cc. to 250 cc. per minute;
   c) transporting the sample to at least one analyzer through an elongated conduit and
   d) further adjusting the vacuum on the sample to maintain a dew point of the sample within a preselected temperature range.

17. The method of claim 16 wherein the sample drawn from the system does not exceed 150 cc./min.

18. The method of claim 16 also comprising the step of measuring a dew point of the sample.

19. The method of claim 16 also comprising the step of removing moisture from the sample prior to drawing the vacuum.

20. The method of claim 19 wherein moisture is removed from the sample by a dryer having a purge line having a purge line critical orifice therein and the sample is drawn through a sample critical orifice, the purge line critical orifice and the sample critical orifice being sized so that a stable ratio is formed between purge flow and sample flow.

21. The method of claim 19 also comprising the step of measuring the moisture removed from the sample.

22. The method of claim 19 wherein at least 99% of the moisture in the sample is removed.

23. The method of claim 19 also comprising the step of measuring a dew point of the sample.

24. The method of claim 16 wherein the sample is transported under vacuum at an absolute pressure of less than 20 millimeters of mercury.

25. The method of claim 24 wherein at least one analyzer is used to withdraw a portion of the sample from the vacuum conduit and to measure at least one constituent of the sample.

26. The method of claim 25 wherein the at least one analyzer is a mass spectrometer.

* * * * *